US008821687B2

(12) United States Patent
Muvundamina et al.

(10) Patent No.: US 8,821,687 B2
(45) Date of Patent: Sep. 2, 2014

(54) FLUSHABLE ARTICLE INCLUDING POLYURETHANE BINDER AND METHOD OF USING THE SAME

(75) Inventors: Mutombo J. Muvundamina, Minneapolis, MN (US); Brian W. Carlson, Woodbury, MN (US)

(73) Assignee: H.B. Fuller Company, St. Paul, MN (US)

( * ) Notice: Subject to any disclaimer, the term of this patent is extended or adjusted under 35 U.S.C. 154(b) by 271 days.

(21) Appl. No.: 13/315,812

(22) Filed: Dec. 9, 2011

(65) Prior Publication Data

US 2012/0160715 A1 Jun. 28, 2012

Related U.S. Application Data

(60) Provisional application No. 61/421,895, filed on Dec. 10, 2010.

(51) Int. Cl.
*D21H 13/14* (2006.01)
*D21H 13/26* (2006.01)
*D21H 17/46* (2006.01)
*D21H 21/18* (2006.01)
*A61L 15/62* (2006.01)
*A61F 13/00* (2006.01)
*C08G 18/00* (2006.01)
*A61F 13/84* (2006.01)
*A61F 13/15* (2006.01)

(52) U.S. Cl.
CPC ............ *A61F 13/15211* (2013.01); *A61F 13/84* (2013.01); *A61F 13/8405* (2013.01)
USPC ....................... 162/157.5; 162/157.3; 162/158; 162/168.1; 162/168.2; 162/231; 162/184; 162/185; 528/59; 427/372.2; 427/385.5

(58) Field of Classification Search
USPC ............. 162/157.1–157.6, 157.3, 158, 168.1, 162/168.2, 231, 183–185; 206/210; 602/41; 604/358; 528/59; 427/372.2, 385.5; 156/296
See application file for complete search history.

(56) References Cited

U.S. PATENT DOCUMENTS

| | | | |
|---|---|---|---|
| 3,846,158 A | 11/1974 | Vasilyadis et al. | |
| 4,002,171 A | 1/1977 | Taft | |
| 4,117,187 A | 9/1978 | Adams et al. | |
| 4,343,403 A * | 8/1982 | Daniels et al. | 206/210 |
| 4,537,807 A | 8/1985 | Chan et al. | |
| 4,578,359 A | 3/1986 | Wells et al. | |
| 5,252,332 A | 10/1993 | Goldstein | |
| 5,494,960 A | 2/1996 | Rolando et al. | |
| 5,500,281 A | 3/1996 | Srinivasan et al. | |
| 5,576,364 A | 3/1996 | Faas et al. | |
| 5,508,101 A * | 4/1996 | Patnode et al. | 442/340 |
| 5,509,913 A * | 4/1996 | Yeo | 604/364 |
| 5,567,510 A * | 10/1996 | Patnode et al. | 442/351 |
| 5,612,438 A | 3/1997 | Raleigh et al. | |
| 5,620,788 A | 4/1997 | Garavaglia et al. | |
| 5,629,081 A | 5/1997 | Richards et al. | |
| 5,667,635 A | 9/1997 | Win et al. | |
| 5,738,646 A | 4/1998 | Fox et al. | |
| 5,770,528 A | 6/1998 | Mumick et al. | |
| 5,905,046 A | 5/1999 | Takeda et al. | |
| 5,907,012 A | 5/1999 | Voss et al. | |
| 5,916,678 A * | 6/1999 | Jackson et al. | 428/373 |
| 5,916,969 A | 6/1999 | Wang et al. | |
| 5,952,251 A | 9/1999 | Jackson et al. | |
| 5,969,052 A | 10/1999 | Mumick et al. | |
| 5,972,805 A | 10/1999 | Pomplun et al. | |
| 5,976,694 A | 11/1999 | Tsai et al. | |
| 5,981,012 A | 11/1999 | Pomplun et al. | |
| 5,986,004 A | 11/1999 | Pomplun et al. | |
| 6,043,317 A | 3/2000 | Mumick et al. | |
| 6,121,170 A | 9/2000 | Tsai et al. | |
| 6,162,328 A * | 12/2000 | Cenisio et al. | 162/135 |
| 6,194,517 B1 | 2/2001 | Pomplun et al. | |
| 6,258,427 B1 | 7/2001 | Kerins et al. | |
| 6,277,768 B1 | 8/2001 | Mumick et al. | |
| 6,287,419 B1 | 9/2001 | Takeuchi et al. | |
| 6,291,372 B1 | 9/2001 | Mumick et al. | |
| 6,294,238 B1 | 9/2001 | Pomplun et al. | |
| 6,384,297 B1 | 5/2002 | Colman et al. | |
| 6,403,706 B1 | 6/2002 | Wang et al. | |
| 6,410,155 B2 | 6/2002 | Mumick et al. | |

(Continued)

FOREIGN PATENT DOCUMENTS

| | | | | |
|---|---|---|---|---|
| AU | 2012101775 | 1/2013 | | |
| EP | 905313 | 3/1999 | | |
| GB | 2284820 | 6/1995 | | |
| JP | 0327195 | 2/1991 | | |
| JP | 03277335 | 12/1991 | | |
| JP | 04370300 | 12/1992 | | |
| JP | 05148799 | 6/1993 | | |
| JP | 10140494 A * | 5/1998 | ............ | D21H 17/27 |
| JP | H10-140494 A | 5/1998 | | |
| JP | 10195797 | 7/1998 | | |
| JP | 11047026 | 2/1999 | | |
| JP | 11047027 | 2/1999 | | |
| JP | 2000005093 | 1/2000 | | |
| JP | 2005194635 | 7/2005 | | |
| JP | 2008073357 | 4/2008 | | |
| WO | WO2006/069119 | 6/2006 | | |
| WO | WO2008/059266 | 5/2008 | | |
| WO | WO2009/138885 | 11/2009 | | |
| WO | WO 2013015735 | 1/2013 | | |

OTHER PUBLICATIONS

Machine translation of JP H10-140494A, Advanced Industrial Property Network, Japan Patent Office, [online], [retrieved on Oct. 31, 2013]. Retrieved from the Internet: <URL: http://dossier1.ipdl.inpit.go.jp/AIPN/odse_top_dn.ipdl?N0000=7400 >.*

(Continued)

*Primary Examiner* — Dennis Cordray
(74) *Attorney, Agent, or Firm* — Kirsten Stone; Allison Johnson

(57) ABSTRACT

A flushable article such as a wipe that includes a substrate that includes fibers, and a dried binder composition in contact with the fibers, the article (e.g., wipe) being insoluble in water having a pH of no greater than 6, and disintegrating in water having a pH of at least 6.5.

41 Claims, No Drawings

(56) References Cited

U.S. PATENT DOCUMENTS

| | | |
|---|---|---|
| 6,410,644 B2 | 6/2002 | Mumick et al. |
| 6,423,804 B1 | 7/2002 | Chang et al. |
| 6,429,261 B1 | 8/2002 | Lang et al. |
| 6,444,214 B1 | 9/2002 | Cole et al. |
| 6,451,429 B2 | 9/2002 | Mumick et al. |
| 6,479,105 B2 | 11/2002 | Campbell et al. |
| 6,495,080 B1 | 12/2002 | Tsai et al. |
| 6,530,910 B1 | 3/2003 | Pomplun et al. |
| 6,533,978 B1 | 3/2003 | Wisneski et al. |
| 6,533,989 B1 | 3/2003 | Wisneski et al. |
| 6,537,663 B1 | 3/2003 | Chang et al. |
| 6,548,592 B1 | 4/2003 | Lang et al. |
| 6,576,575 B2 | 6/2003 | Griesbach et al. |
| 6,579,570 B1 | 6/2003 | Lang et al. |
| 6,586,529 B2 | 7/2003 | Mumick et al. |
| 6,596,920 B2 | 7/2003 | Wehner et al. |
| 6,599,848 B1 | 7/2003 | Chen et al. |
| 6,602,955 B2 | 8/2003 | Soerens et al. |
| 6,607,819 B2 | 8/2003 | Li et al. |
| 6,630,558 B2 | 10/2003 | Chang et al. |
| 6,638,603 B1 | 10/2003 | Kerins et al. |
| 6,664,333 B2 | 12/2003 | Wang et al. |
| 6,683,143 B1 | 1/2004 | Mumick et al. |
| 6,713,140 B2 | 3/2004 | McCormack et al. |
| 6,713,414 B1 | 3/2004 | Pomplun et al. |
| 6,783,826 B2 | 8/2004 | Sherrod et al. |
| 6,814,974 B2 | 11/2004 | Cole et al. |
| 6,815,502 B1 | 11/2004 | Lang et al. |
| 6,828,014 B2 | 12/2004 | Chang et al. |
| 6,835,678 B2 | 12/2004 | Jackson et al. |
| 6,855,790 B2 | 2/2005 | Chang et al. |
| 6,897,168 B2 | 5/2005 | Branham et al. |
| 6,908,966 B2 | 6/2005 | Chang et al. |
| 6,960,371 B2 | 11/2005 | Bunyard et al. |
| 6,994,865 B2 | 2/2006 | Branham et al. |
| 7,070,854 B2 | 7/2006 | Chang et al. |
| 7,101,456 B2 | 9/2006 | Bunyard et al. |
| 7,101,612 B2 | 9/2006 | Lang et al. |
| 7,141,519 B2 | 11/2006 | Bunyard et al. |
| 7,157,389 B2 | 1/2007 | Branham et al. |
| 7,276,459 B1 | 10/2007 | Lang et al. |
| 7,285,504 B2 | 10/2007 | Jones et al. |
| 7,378,360 B2 | 5/2008 | Clark et al. |
| 7,456,117 B2 | 11/2008 | Branham et al. |
| 7,589,149 B2 | 9/2009 | Kim et al. |
| 7,605,096 B2 | 10/2009 | Tomarchio et al. |
| 2001/0008824 A1* | 7/2001 | Rhim et al. .................. 442/329 |
| 2003/0118767 A1 | 6/2003 | Krzysik et al. |
| 2004/0126585 A1* | 7/2004 | Kerins et al. ............... 428/411.1 |
| 2006/0003649 A1 | 1/2006 | Runge et al. |
| 2012/0144611 A1 | 6/2012 | Baker et al. |
| 2012/0160436 A1 | 6/2012 | Zwick et al. |
| 2012/0199301 A1 | 8/2012 | Strandqvist |

OTHER PUBLICATIONS

Technical Data sheet for Boric Acid , Manufacturas Los Andes, no date, [online], Retrieved from the Internet, [retrieved Feb. 13, 2014], <URL: http://www.mandes.com.ar/technic-boric-acid.php>.*

* cited by examiner

FLUSHABLE ARTICLE INCLUDING POLYURETHANE BINDER AND METHOD OF USING THE SAME

CROSS-REFERENCE TO RELATED APPLICATIONS

This application claims priority to U.S. Provisional Application No. 61/421,895, filed Dec. 10, 2010, and incorporated herein.

BACKGROUND

The invention relates to disintegrating substrates such as wipes.

Efforts have been made to develop disposable products such as diapers and personal care items that can be discarded by flushing them down a toilet. One area of focus in this effort has been the binder that is used to bind together the fibers that are used in disposable products. The binder must have sufficient strength to hold the fibers together during storage and use yet lose strength when placed in water.

Binders that have been proposed for this purpose have been formulated with polymers that are soluble in cold water, such as the water found in a toilet, but insoluble in warm water. Other binders have been formulated with polymers that are sensitive to ions. The ion-sensitive polymers, when placed in an aqueous medium, are sensitive to a change in the concentration of ions in the aqueous medium. Some ion sensitive polymers are insoluble in aqueous solutions that have a high concentration of salt but soluble in aqueous solutions that have a low concentration of salt. The theory is that if the polymer is soluble in a solution with a low concentration of salt, such as water, then the polymer will dissolve once it is in contact with water. If the binder dissolves, then it will no longer be able to function as a binder and will lose its "binding" properties. As a result, an article constructed with such a binder may break apart when placed in toilet water and be capable of being flushed down the toilet.

SUMMARY

In one aspect, the invention features a flushable article that includes a substrate that includes fibers, and a dried binder composition in contact with the fibers, the article being insoluble in water having a pH of no greater than 6 and disintegrating in water having a pH of at least 6.5. In some embodiments, the article is in the form of a flushable wipe that includes the substrate that includes fibers, and the dried binder composition in contact with the fibers, the wipe being insoluble in water having a pH of no greater than 6, and disintegrating in water having a pH of at least 6.5.

In some embodiments, the dried binder composition is insoluble in water having a pH of no greater than 6 and disintegrates in water having a pH of at least 6.5. In other embodiments, the dried binder composition exhibits a loss in integrity relative to its initial state, a decrease in cohesive strength relative to its initial state, or a combination thereof in water having a pH of at least 6.5. In one embodiment, the dried binder composition is insoluble in water having a pH of no greater than 5.5. In another embodiment, the dried binder composition is insoluble in water having a pH of no greater than 5. In some embodiments, the dried binder composition disintegrates in water having a pH of at least 7.

In other embodiments, the substrate is saturated with the binder composition such that the dried binder composition is present on the fibers and in interstices between the fibers.

In one embodiment, the wipe further includes an aqueous medium in contact with the substrate, the medium having a pH no greater than 6. In other embodiments, the medium includes a lotion. In some embodiments, the fibers include at least one of wood pulp, cellulose, polyethylene, polypropylene, polyester, polyamide, and polylactic acid.

In some embodiments, the substrate includes multiple layers. In one embodiment, the substrate includes a first layer that includes fibers oriented in a first direction, and a second layer that includes fibers oriented in a second direction different from the first direction.

In another embodiment, the wipe includes at least 5% by weight dried binder composition based on the weight of the binder and the substrate. In other embodiments, the wipe includes from about 10% by weight to about 25% by weight dried binder composition based on the weight of the binder and the substrate.

In some embodiments, the dried binder composition is insoluble in water having a pH no greater than 5.5.

In one embodiment, the dried binder composition is derived from an anionic polyurethane dispersion. In one embodiment, the dried binder composition includes a polyurethane that includes the reaction product of a polyurethane prepolymer, a chain extending agent that includes a polyamine, and a chain terminating agent that includes a monoamine. In other embodiments, the dried binder composition includes a polyurethane that includes the reaction product of an acid-functional polyurethane prepolymer, a chain extending agent that includes a polyamine, and a chain terminating agent comprising a monoamine.

In another embodiment, the dried binder composition includes a polyurethane that includes the reaction product of an acid-functional polyurethane prepolymer at least a portion of which is in a form selected from the group consisting of an alkali metal salt, a salt of a tertiary amine, an ammonium salt, and combinations thereof, a chain extending agent comprising a polyamine, and a chain terminating agent that includes a monoamine.

In another embodiment, the dried binder composition includes a polyurethane that includes the reaction product of a polyurethane prepolymer, an alkylene polyamine, and an alkanolamine. In other embodiments, the dried binder composition includes a polyurethane that includes the reaction product of polyurethane prepolymer, a polyamine, a monoamine, and a tertiary amine. In some embodiments, the polyurethane prepolymer includes the reaction product of polymeric polyol, dihydroxy acid, and polyisocyanate. In other embodiments, the dihydroxy acid includes dimethylolpropionic acid and the polyisocyanate includes isophorone diisocyanate. In another embodiment, the dihydroxy acid includes the reaction product of a trifunctional polyol and phthalic anhydride.

In one embodiment, the polyurethane prepolymer has an acid number of at least 10.

In another embodiment, the polyurethane prepolymer has a residual isocyanate functionality of from 2% by weight to 6% by weight and the dried binder composition is formed from the monoamine in an amount such that the ratio of amine groups in the monoamine to isocyanate groups in the polyurethane prepolymer is from 0.01:1 to 0.8:1.

In other aspects, the invention features a flushable wipe that includes a substrate that includes fibers and a dried binder composition in contact with the fibers, the dried binder composition including a polyurethane polymer, the wipe being insoluble in water having a pH greater than 6.5 and disintegrating when tested according to the wipe disintegration method. In one embodiment, the polyurethane polymer is an anionic polyurethane polymer. In some embodiments, the anionic polyurethane polymer, when dry, is insoluble in water having a pH less than 6 and disintegrates in water having a pH of at least 6.5.

In another aspect, the invention features a packaged article that includes a container, an aqueous medium disposed in the container, and a wipe described herein disposed in the container and saturated with the aqueous medium.

In other aspects, the invention features a method of making a flushable article, the method including applying an aqueous binder composition disclosed herein on at least one of fibers and a substrate comprising fibers, the binder composition, when dry, being insoluble in water having a pH no greater than 6 and disintegrating in water having a pH greater than 6.5, if the fibers are not in the form of a substrate, forming a substrate from the fibers, and drying the binder composition. In one embodiment, the article disintegrates in tap water when tested according to the Substrate Integrity test method. In another embodiment, the method further includes contacting the substrate with an aqueous medium having a pH no greater than 6. In one embodiment, the aqueous binder composition includes a first anionic polyurethane dispersion that includes the reaction product of a polyurethane prepolymer, a polyamine, and a monoamine. In other embodiments, the aqueous binder composition further includes a second anionic polyurethane dispersion that includes an alkali metal salt of a sulfonic acid. In some embodiments, the article is a wipe and the substrate is a sheet.

In one embodiment, method is a method of making a flushable wipe, the method including applying an aqueous binder composition disclosed herein to at least one of fibers and a substrate that includes fibers, the binder composition, when dry, being insoluble in water having a pH no greater than 6 and disintegrating in water having a pH greater than 6.5, and where the binder is applied to fibers, the method further including forming the fibers into a substrate. In some embodiments, the method further includes applying the aqueous binder composition to the substrate. In another embodiment, the method further includes drying the binder composition. In other embodiments, the fibers are in the form of the substrate prior to applying the aqueous binder composition. In one embodiment of the method, the aqueous binder composition includes a polyurethane disclosed herein. In another embodiment, the method further includes contacting the substrate with a medium having a pH no greater than 6. In some embodiments, the medium includes an aqueous liquid.

In another aspect, the invention features a flushable article that includes a substrate that includes fibers, and a dried binder composition in contact with the fibers, the dried binder composition being insoluble in water having a pH of no greater than 6 and disintegrating in water having a pH of at least 6.5. In one embodiment, the dried binder is insoluble in water having a pH of no greater than 5.5. In other embodiments, the dried binder disintegrates in water having a pH of at least 7.

In one embodiment, the article is a multi-component article that includes an article described herein and is in the form of a diaper, sanitary napkin, sheet, training pants, incontinence articles, a container, filter, ostomy bag, garment, surgical gown, face mask, insert for an absorbent article, shoe insert, antiperspirant patch, breast pad, helmet liner, wound dressing, sterile wrap, automobile cover, ground cover, blanket, table cloth, or a combination thereof.

In another aspect, the invention features a flushable article that includes a substrate that includes fibers, and a dried binder composition in contact with the fibers, the dried binder composition being insoluble in water having a pH of no greater than 6, and, when tested in tap water according to the Dry Binder Integrity Test Method I, disintegrates, loses its integrity relative to its initial state, decreases in cohesive strength relative to its initial state, or a combination thereof.

In other aspects, the invention features a dried binder composition that includes the reaction product of a polyurethane prepolymer, a chain extending agent comprising a polyamine, and a chain terminating agent comprising a monoamine, the dried binder composition being in a form selected from the group consisting of fibers, filaments, granules, particles, powder, or a combination thereof, and being insoluble in water having a pH of no greater than 6 and disintegrating in water having a pH of at least 6.5.

The invention features a wipe that maintains its integrity during storage and use and disintegrates when placed in water having a pH of at least 6.5. The invention also features an article that maintains its integrity in water at a pH of no greater than 6 and disintegrates when placed in water having a pH of at least 6.5.

Other features and advantages will be apparent from the following description of the preferred embodiments and from the claims.

GLOSSARY

In reference to the invention, these terms have the meanings set forth below:

The term "disintegrates" means breaks apart.

The term "flushable" means an article that disintegrates, crumbles, exhibits a loss in integrity, or a combination thereof when tested according to the Tap Water Wipe Integrity Test Method or the Tap Water Substrate Integrity Test Method.

The term "water having a pH of no greater than" means an aqueous solution prepared by adding citric acid and sodium citrate to deionized water in amounts sufficient to create a buffered solution having a pH no greater than the specified value.

DETAILED DESCRIPTION

The flushable article (e.g., wipe) includes a substrate (e.g., a sheet) that includes fibers and a dried binder composition in contact with the fibers. The flushable article maintains its integrity and strength (e.g., does not disintegrate) while stored in water having a pH no greater than 6, and disintegrates in water having a pH greater than 6.5. A substrate that disintegrates at a pH greater than 6.5 may not disintegrate at a pH of 6.6, but may disintegrate at a pH of about 7, at least 7.5, or even at least 8. One method of determining whether a substrate maintains its integrity in water having a pH no greater than 6 and disintegrates in water having a pH greater than 6.5 is the Substrate Integrity test method set forth herein.

For ease of reference, the article is referred to hereinafter as a wipe; however, it is to be understood that the statements pertaining to a wipe apply equally to an article. The flushable wipe also maintains its integrity and strength (e.g., does not disintegrate) while stored in water having a pH no greater than 6, and disintegrates in water having a pH greater than 6.5. A wipe that disintegrates at a pH greater than 6.5 may not disintegrate at a pH of 6.6, but may disintegrate at a pH of about 7, at least 7.5, or even at least 8. One method of determining whether a wipe maintains its integrity in water having a pH no greater than 6 and disintegrates in water having a pH greater than 6.5 is the Wipe Integrity test method set forth herein. The wipe is optionally stored in a storage medium that can assist in maintaining the integrity of the wipe until the wipe is discarded.

The substrate is formed from fibers derived from a variety of sources including, e.g., wood pulp, cotton, linen, jute, hemp, wool, cellulose, cellulose acetate, viscose rayon, polyolefins (e.g., polyethylene and polypropylene), polyester, polyamide, polyacrylics, polylactic acid, and combinations thereof. The fibers can be formed from a variety of processes including, e.g., extruding, carding, melt blowing, spun bonding, staple carding, film aperturing, pulping, and combinations thereof. The fibers can have any dimension including, e.g., short fibers having a length of no greater than 30 millimeters, long filaments, and combinations thereof.

The fibers can be formed into a substrate having a variety of forms including, e.g., a sheet, a roll, a mat (e.g., an air laid mat and a wet laid mat), a pad, tissue (e.g., creped tissue and uncreped tissue), a nonwoven web, a coform product, a hydroentangled web, and combinations and composites thereof. The substrates can be formed using any suitable process including, e.g., air laid process, wet laid process, staple fiber carding, hydroentangling process, stable fiber bonding, and solution spinning.

The substrate can be in the form of a single layer or multiple layers, and have any suitable density. The fibers in the substrate can be oriented in a variety of configurations including, e.g., in one direction, in multiple directions, randomly, and combinations thereof, and, where multiple layers are present, the layers can include a variety of constructions including, e.g., a layer that includes fibers oriented in a first direction, a layer that includes fibers oriented in a second direction, a layer that includes fibers oriented in a third direction, a layer that includes randomly oriented fibers, and combinations thereof. The substrate can also include texture, e.g., embossed texture (e.g., dimples and lines (e.g., linear and curved)), abrasives, quilting, pleats, and combinations thereof.

The dried binder composition of the wipe includes the reaction product of a polyurethane prepolymer, and optionally a monoamine chain a polyamine chain extender, and combinations thereof. The dried binder composition is formed from an aqueous polyurethane dispersion (i.e., the aqueous binder composition) that is applied to the fibers of the substrate, the substrate, or a combination thereof, and, dried. The dried binder composition maintains the fibers of the substrate of the wipe in a fixed relation to one another. The integrity of the dried binder composition changes in response to a change in pH. The dried binder composition is insoluble in water having a pH of no greater than 6. In water having a pH of at least 6.5, the dried binder composition can exhibit various properties including, e.g., disintegrating, losing its integrity relative to its initial state, exhibiting a decrease in cohesive strength relative to its initial state, and combinations thereof. Two methods for determining whether a dried binder composition is insoluble in water having a pH no greater than 6 and disintegrates in water having a pH greater than 6.5 are the Dry Binder Integrity Test Methods I and II set forth herein.

The amount of dried binder composition present in the wipe, i.e. the "add on", can be any suitable amount. Useful dried binder add on results in a wipe that includes at least 5% by weight, at least 10% by weight, at least 20% by weight, or even from about 10% by weight to about 25% by weight dried binder based on the total dry weight of the wipe.

The aqueous binder composition from which the dried binder composition is derived includes an anionic polyurethane dispersion that includes the reaction product of an acid functional polyurethane prepolymer, a monoamine chain terminator, and a polyamine chain extender. The aqueous binder composition has a pH of from about 7 to about 8.7 or even from about 7.1 to about 8.2, and can be formulated to exhibit any desired viscosity including, e.g., a viscosity suitable for spraying. Useful aqueous binder compositions have a viscosity no greater than 1000 centipoise (cP), no greater than 500 cP, no greater than 250 cP, no greater than 100 cP, or even no greater than 50 cP, when measured at room temperature, i.e., 77° F. (25° C.). The aqueous binder composition includes at least 20% by weight solids, no greater than about 65% by weight solids, from about 25% by weight solids to about 60% by weight solids, from about 30% by weight solids to about 55% by weight solids, or even from about 30% by weight solids to about 50% by weight solids. The aqueous binder composition preferably includes at least 60% by weight, at least 65% by weight, at least 70% by weight, at least 75% by weight, at least 80% by weight, at least 90% by weight at least 95% by weight or even at least 100% by weight of an anionic polyurethane dispersion.

Acid functional polyurethane prepolymers suitable for use in the polyurethane dispersion of the aqueous binder composition are water dispersible and have an average isocyanate functionality (i.e., average number of functional groups) of at least about 1.8, at least about 2.0, or even no greater than about 3.0. The polyurethane prepolymer has an isocyanate content of from about 2% by weight to about 6% by weight, from about 2% by weight to about 5.5% by weight, or even from about 2.25% by weight to about 5% by weight, and an acid number less than 30, from about 10 to less than 30, from about 15 to about 27, or even from about 15 to about 25, as determined by ASTM D-1639-90. The acid functional polyurethane prepolymer is the reaction product of an acid functional component, a polymeric polyol, a polyisocyanate, and optionally a neutralizing agent, a catalyst, or a combination thereof.

The acid functional component and the polymeric polyol can be present on the same compound (i.e., the polyol can have acid functionality); alternatively or in addition, the polyol and the acid functional component can be two separate compounds. The acid functional component includes at least one acid group, e.g., carboxylic acid, sulfonic acid, and combinations thereof. Examples of useful acids include dihydroxycarboxylic acids, dihydroxysulfonic acids, diaminocarboxylic acids and diaminosulfonic acids, dimethylolpropionic acid, glycolic acid, thioglycolic acid, lactic acid, malic acid, dihydroxymalic acid, tartaric acid, dihydroxytartaric acid, 2,6-dihydroxybenzoic acid, oxaluric acid, anilidoacetic acid, glycine, α-alanine, 6-aminocaproic acid, the reaction product of ethanolamine and acrylic acid, hydroxyethylpropionic acid, 2-hydroxyethanesulfonic acid, sulphanilic acid, and combinations thereof.

The acid functional component optionally is provided in the form of an alkali metal salt (e.g., sodium and potassium), useful examples of which include an alkali metal salt of a sulfonic acid, an alkali metal salt of a carboxylic acid, and combinations thereof.

The acid functional component optionally includes at least one functional group (or even at least two functional groups) reactive with an isocyanate group, examples of which include hydroxyl groups, amine groups, thiol groups, and combinations thereof. Suitable acid functional components that include additional functionality include, e.g., hydroxy carboxylic acids, mercapto carboxylic acids, amino carboxylic acids, aminohydroxy carboxylic acids, hydroxysulfonic acids, amino sulfonic acids, aminohydroxy sulfonic acids, and combinations thereof.

Useful acid functional polyols have at least two hydroxyl functional groups and at least one acid functional group. A variety of acid functional polyols are suitable including, e.g., acid grafted polyols (e.g., acid grafted polyether polyol (e.g., polyether diols and triols derived from ethylene oxide polymers, propylene oxide polymers, and combinations thereof grafted with acid, e.g., maleic acid and fumaric acid)), polyether polyols formed from a trifunctional polyether polyol and a phthalic anhydride, polyester polyols produced from mixtures of compounds that include at least two acid functional groups (e.g., di- and tri-acids (e.g., dicarboxylic acid)) and at least two hydroxyl groups such that the resulting polyester polyol has residual acid functionality and at least two hydroxyl groups, and combinations thereof.

Polymeric polyols useful in forming the polyurethane prepolymer include, e.g., polyester polyols, polyether polyols, polycarbonate polyols, polyurethane polyols, polyacetal polyols, polyacrylate polyols, polycaprolactone polyols, polyesterether polyols, amide-containing polyols, and the anionic polymeric polyols described in U.S. Pat. No. 5,334,690 issued to Hoechst Aktiengesellschaft, Fed. (Germany). Suitable polymeric polyols have an average of at least two, at least three, at least four, or even at least five hydroxyl groups per molecule (e.g., diols, triols, tetrols, and pentols), a molecular weight of from about 500 to about 12,000, or even from about 1,000 to about 2,000, and an average hydroxyl value from about 10 to about 2000, from about 20 to 1500, or even from about 25 to about 500. As indicated above in the discussion pertaining to the acid component, the polymeric polyol can include a variety of functional groups including, e.g., acid, hydroxy, amine, and thiol groups, and combinations thereof.

Particularly useful polymeric polyols include, e.g., polyalkylene ether polyols (e.g., thioethers, poly(oxytetramethylene)glycols, polyoxyethylene)glycols, polypropylene glycols, and the reaction product of ethylene glycol with a mixture of propylene oxide and ethylene oxide), polyester polyols (e.g., polyhydroxy polyesteramides and hydroxyl containing polycaprolactones), hydroxy-containing acrylic interpolymers, and combinations thereof.

Useful polymeric polyether polyols include polyether polyols formed from the oxyalkylation of various polyols including, e.g., glycols (e.g., ethylene glycol, butylene glycol, 1,6-hexanediol, and neopentyl glycol), Bisphenol A, hydroxyalkylated bisphenols, cyclohexane diol, cyclohexane dimethanol, caprolactone diol (e.g., the reaction product of caprolactone and ethylene glycol), polyols of higher functionality (e.g., trimethylol ethane, trimethylol propane, glycerol, pentaerythritol, and polyols prepared by oxyalkylation of compounds as sorbitol and sucrose), and combinations thereof. One commonly utilized oxyalkylation method includes reacting a polyol with an alkylene oxide (e.g., propylene oxide, or propylene oxide followed by ethylene oxide) in the presence of a catalyst.

Useful polymeric polyhydric polythioethers include, e.g., the condensation product of thioglycol and the reaction product of a polyhydric alcohol.

Useful polymeric polyester polyols are prepared by the polyesterification of organic polycarboxylic acids (or anhydrides thereof) with organic polyols. Polycarboxylic acids useful in forming polyester polyols include aliphatic and aromatic dibasic acids. Polyols useful in forming polyester polyols include diols and higher functional polyols (useful examples of both of which are described above). Additional examples of diols suitable for use in making the polyester polyol include, e.g., glycols, alkylene glycols (e.g., ethylene glycol, butylene glycol, and neopentyl glycol), hydrogenated Bisphenol A, cyclohexane diol, cyclohexane dimethanol, caprolactone diol (e.g., the reaction product of caprolactone and ethylene glycol), hydroxyalkylated bisphenols, polyether glycols (e.g., poly(oxytetramethylene)glycol), and combinations thereof. Higher functional polyols suitable for use in forming polyester polyols include, e.g., trimethylolethane, trimethylolpropane, pentaerythritol, glycerol, polyols prepared by oxyalkylating low molecular weight polyols (e.g., the reaction product of 20 moles of ethylene oxide per mole of trimethylol propane), and combinations thereof.

The polyurethane prepolymer also can be prepared from a small amount of aliphatic polyol in addition to the polymeric polyol. Such aliphatic polyols include, e.g., alkylene polyols diols, triols, and tetraols) having from 2 to 18 carbon atoms. Useful alkylene diols have a hydroxy number of from about 100 to about 1250, or even from about 950 to about 1250. Examples of useful diols include ethylene glycol, diethylene glycol, triethylene glycol, tetraethylene glycol, oxyalkylated glycerol, 1,4-butanediol, 1,6-hexanediol, cycloaliphatic polyols (e.g., 1,2 cyclohexanediol and cyclohexane dimethanol), furan dimethanol, glycerol, bis-(dihydroxyethyl) lauramide, polyethylene ether glycols, poly-1,2-propylene ether glycols, polytetramethylene ether glycols, poly-1,2-dimethylethylene ether, and combinations thereof. Useful triols and higher order polyhydroxyls include, e.g., trimethylol ethane, trimethylol propane, glycerol, and pentaerythritol.

The polyurethane prepolymer can be prepared from 0% by weight to about 5.0% by weight, form 0.1% by weight to about 5.0% by weight, or even from about 1.0% by weight to about 4.0% by weight of the optional aliphatic polyol based the weight of the prepolymer.

Useful polyisocyanates include, e.g., monomeric diisocyanates, homologs of monomeric diisocyanates, modified diisocyanates (e.g., carbodiimide-modified isocyanates, allophanate-modified isocyanates, biuret modified isocyanates, and trimerized isocyanates), and higher order isocyanates including triisocyanates, and combinations thereof. Useful classes of isocyanates include, e.g., linear aliphatic, cyclic aliphatic, araliphatic, and aromatic diisocyanates, and combinations thereof. Examples of suitable diisocyanates include hexane diisocyanate, 2,4,4-trimethylhexamethylene diisocyanate, 2,2,4-trimethylhexamethylene diisocyanate, 4,4'-methylenebis(cyclohexyl isocyanate), 2,4'-methylenebis(cyclohexyl isocyanate), 2,2'-methylenebis(cyclohexyl isocyanate), 4,4'-diphenylmethane diisocyanate, 2,4'-diphenylmethane diisocyanate, 2,2'-diphenylmethane diisocyanate, 2,4'-toluene diisocyanate, 2,6'-toluene diisocyanate, isophorone diisocyanate, 1,3-tetramethylxylylene diisocyanate, 1,4-tetramethylxylylene diisocyanate, and mixtures thereof.

The components used to form the polyurethane prepolymer optionally include a neutralizing agent. The neutralizing agent neutralizes the acid groups of the acid component used in the formation of the polyurethane prepolymer. The neutralizing agent is any suitable tertiary amine. Neutralization of the acid groups to ionic groups (i.e., salts) can occur at any point during the preparation of either the polyurethane prepolymer or the polyurethane dispersion including, e.g., prior to the condensation reaction that forms the polyurethane prepolymer, immediately before the polyurethane prepolymer is dispersed in water, after the polyurethane prepolymer is dispersed in water, and combinations thereof. When the acid groups are neutralized after the prepolymer is dispersed in water, the neutralizing agent can be a tertiary amine, ammonia, and combinations thereof. Useful tertiary amines include, e.g., trimethylamine, triethylamine, tri-n-propyl amine, tri-n-butyl amine, n-methylpiperidine, n-ethylpiperidine, n-methylpyrrolidine, methyldiethylamine, dimethylethylamine, ethyldipropylamine, and combinations thereof.

The tertiary amine can be present in an amount sufficient to neutralize at least 50% of the acid groups, from about 85% to 100% of the acid groups, from about 85% to 95% of the acid groups, or even from about 90% to about 95% of the acid groups.

In addition or alternatively, a neutralizing agent can optionally be added to the aqueous mixture used to form the binder composition. Examples of neutralizing agents suitable for addition to the aqueous mixture used to form the binder composition include ammonia, alkali metal hydroxides (e.g., sodium hydroxide and potassium hydroxide) and the neutralizing agents discussed above in reference to the formation of the polyurethane prepolymer, i.e., tertiary amines. When ammonia or an alkali metal hydroxide is used as the neutralizing agent, it can be present in the mixture used to form the binder composition an amount sufficient to neutralize from at least 50% to 100% of the acid groups, from about 60% to about 95% of the acid groups, or even from about 70% to about 95% of the acid groups of the polyurethane prepolymer.

A neutralizing agent (e.g., the neutralizing agents described above) can also be added to the binder composition, the mixture used to form the polyurethane prepolymer, or both compositions, to adjust the pH of the resulting binder composition. A suitable amount of neutralizing agent is an amount sufficient to modify the pH of the binder composition to a pH of from about 7 to about 8.7, or even from about 7.1 to about 8.2.

The reaction mixture used to form the polyurethane prepolymer optionally includes a catalyst. Useful catalysts include, e.g., organotin, (e.g., dibutyltindilaurate and tin octoate), and tertiary amines.

The chain terminator in the aqueous binder composition is water soluble. Useful water soluble chain terminators include monoamines including, e.g., aliphatic monoamines, aromatic monoamines, and mixtures thereof. Useful monoamines include, e.g., alkanolamines (e.g., monoethanolamine, monomethanolamine, dimethanolamine, and diethanolamine). The chain terminator is present in the aqueous binder composition at an equivalence ratio of amine active hydrogen to isocyanate of from about 0.01:1.0 to about 0.8:1.0, or even from about 0.05:1.0 to about 0.5:1.0.

A chain extender suitable for use in the aqueous binder composition is a polyamine. Suitable classes of polyamines include, e.g., diamines, triamines, tetramines, and combinations thereof. Examples of useful polyamines include hydrazine, substituted hydrazines, ethylene diamine, propylene diamine, butylene diamine, hexamethylene diamine, cyclohexylene diamine, piperazine, 2-methyl piperazine, phenylene diamine, tolylene diamine, xylyldiamine, tris(2-aminoethyl)amine, dialkylene triamines (e.g., dimethylene triamine and diethylene triamine), triethylene tetramine, tetraethylene pentamine, and combinations thereof. The chain extender is present in the aqueous binder composition at an equivalence ratio of amine active hydrogen to isocyanate in a range from about 0.1:1.0 to about 0.9:1.0, and from about 0.4:1.0 to about 0.8:1.0.

The aqueous binder composition optionally includes a variety of other additives including, e.g., additional polymers, preservatives, color agents, surfactants, defoaming agents, fungicides, bactericides, thickening agents, and combinations thereof.

Examples of useful additional polymers include additional anionic polyurethane dispersions (e.g., a second anionic polyurethane dispersion different from the first polyurethane dispersion), polyacrylate, polyacrylamide, copolymers of acrylamide and acrylic acid, polyvinyl alcohol, polyvinyl acetate, partially de-esterified polyvinyl acetate, sulfonated polyesters, phosphonated polyesters, and combinations thereof. The additional polymer, when present, is preferably present in an amount less than 50% by weight of the aqueous binder composition.

One example of a useful class of second polyurethanes includes anionic polyester polyurethanes dispersions that include an alkali metal salt of an acid, including, e.g., an alkali metal salt of sulfonic acid, an alkali metal salt of a carboxylic acid, and combinations thereof in the backbone of the polyurethane. Suitable alkali metal salts include, e.g., sodium and potassium. Examples of useful anionic polyester polyurethane dispersions include a sodium salt of sulfonic acid anionic polyester polyurethane dispersion, a potassium salt of sulfonic acid anionic polyester polyurethane dispersion, a sodium salt of carboxylic acid anionic polyester polyurethane dispersion, a potassium salt of carboxylic acid anionic polyester polyurethane dispersion, and combinations thereof. One example of a useful commercially available anionic polyester polyurethane dispersion is BAYBOND PU330 from Bayer Material Sciences (Pittsburgh, Pa.).

When at least one second anionic polyurethane dispersion is present, it preferably is present in the aqueous binder composition in an amount of less than 45% by weight, less than 40% by weight, no greater than 35%, no greater than 30%, at least 0.5% by weight, at least 2.5% by weight, at least about 5% by weight, at least about 10% by weight, or even from about 5% by weight to about 30% by weight.

Examples of useful preservatives include formaldehyde, 1,2-benzisothiazol-3(2H)-one, 1-[(diiodomethyl)sulfonyl]-4-methyl-benzene, 5-chloro-2-methyl-3(2H)-isothiazolone, and combinations thereof.

The wipe can be prepared using any suitable technique including, e.g., contacting the fibers or the fibrous substrate with the aqueous binder composition, optionally forming the fibers into a substrate when the fibers are not in the form of a substrate, and drying the binder composition. Useful processes for applying the aqueous binder composition on the fibers or the fibrous substrate include, e.g., printing, brushing, spraying, electrostatic spraying, coating, impregnating, immersing (e.g., saturating), roll coating (e.g., metered press rolls and flooded nips), and combinations thereof. The binder composition can be present on the wipe in a variety of configurations including, e.g., on at least one surface of the substrate, throughout the fibrous substrate (e.g., impregnated in the substrate such that the binder is present on the fibers and in the interstitial spaces between the fibers (e.g., the substrate is saturated with the binder composition)), and combinations thereof, uniformly, non-uniformly, as a continuous coating, as a discontinuous coating, and combinations thereof. The binder composition can be dried using any suitable process including, e.g., air drying, drying at an elevated temperature (e.g., at least about 120° C., at least about 130° C., or even at least about 150° C.), drying at an elevated temperature in a controlled environment, and combinations thereof.

The wipe optionally includes a storage medium that is retained within the fibrous substrate until the wipe is used by a user. The storage medium has a pH no greater than 6, no greater than 5.5, no greater than 5, from about 3.5 to about 6, or even from about 3.5 to 5.5. The storage medium can be in a variety of forms including, e.g., a liquid and a paste. The fibrous substrate can be saturated with the medium such that the medium permeates the fibers and the interstitial spaces between the fibers. The storage medium is selected to enable the integrity of the dried binder to be maintained such that the wipe does not disintegrate. The dried hinder is insoluble in the storage medium.

The medium can be associated with the substrate in a variety of ways including, e.g., as a coating on at least one surface of the substrate, impregnated in the substrate such that the medium is present on the fibers and in the interstitial spaces between the fibers (e.g., the substrate is saturated with the medium), and combinations thereof. The wipe can be contacted with the medium using a number of processes including, e.g., impregnating, immersing, brushing, printing, roll coating, spraying, and combinations thereof. The medium can provide a variety of functions including, e.g., a storage medium for the wipe, an active agent to be applied from the wipe when a user uses the wipe, and combinations thereof.

A variety of components can be included in the medium including, e.g., water, isopropyl alcohol, lotions (e.g., lotions that include dimethicone, surfactants, soaps, stearic acid, cetyl alcohol, lanolin, triethanolamine, glycerol, propylene glycol, aloe barbadensis leaf juice, tocopheryl acetate, PEG 75 polyethylene glycol, lanolin, disodium cocoamphodiacetate, polysorbate 20, methylisothiazolinone, 2-bromo-2-nitropropane-1,3-diol, and iodopropynyl butylcarbamate, and combinations thereof), softeners, acids (e.g., boric acid and citric acid), salt solutions (e.g., potassium chloride, sodium chloride, zinc sulfate, and sodium borate), antibacterial agents, anti-acne agents, fragrance, preservatives, emollients, humectants, detergents, soaps, antiviral agents, antimicrobial agents, disinfectants, antifungal agents, and combinations thereof. The medium can include a variety of additives including, e.g., skin care additives, odor control additives, detackifying agents, microparticulates, delivery vehicles ((e.g., including microcapsules) for providing a variety of agents including, e.g., skin-care agents, medications, comfort promoting agents (e.g., eucalyptus oil, camphor oil, and aloe vera extracts), perfumes, odor control additives, vitamins, powders, and other components, to the skin of a user), preservatives, anti-microbial agents, wetting agents (e.g., surfactants), cleaning agents, aqueous microemulsions of silicone particles, emollients, surface feel modifiers for improving the tactile sensation (e.g., lubricity) experienced by the skin during use of the product, fragrances, fragrance solubilizers, opacifiers, and combinations thereof.

Useful skin care additives that can be included in the medium include, e.g., enzyme inhibitors, sequestrants, antimicrobial agents, sun blocking agents, UV absorbers, acne treatments, pharmaceuticals, baking soda (including encapsulated forms thereof), vitamins and their derivatives (e.g., Vitamins A and E), botanicals (e.g., witch hazel extract and aloe vera), allantoin, emollients, disinfectants, hydroxy acids for wrinkle control or anti-aging effects, sunscreens, tanning promoters, skin lighteners, deodorants, anti-perspirants, ceramides, astringents, moisturizers, nail polish removers, insect repellants, antioxidants, antiseptics, anti-inflammatory agents, and combinations thereof.

The medium optionally includes a pH control agent. Suitable pH control agents include, e.g., malic acid, citric acid, hydrochloric acid, acetic acid, sodium hydroxide, potassium hydroxide, and combinations thereof. Where the wipe is to be used for applications in which pH sensitivity may exist, the pH of the medium can be selected to minimize or maximize the sensitivity depending upon the purpose of the wipe, e.g., for skin applications the pH can be selected to minimize the amount of skin irritation resulting from the wetting composition being in contact with the skin. Useful media have a pH less than 6.5, less than 6, no greater than about 5, from about 3.6 to about 5, or even from about 4 to about 5.

The wipe is suitable for a variety of uses and purposes including, e.g., personal hygiene (e.g., cleaning and treating skin, make-up removal, nail polish removal), medical uses (e.g., cleaning and treating wounds and incisions, and pain relief), pet care (e.g., eye, ear, and dental cleansing), household use including, e.g., cleaning surfaces (e.g., bathroom surfaces, kitchen surfaces, laundry room surfaces, garage surfaces, and automotive surfaces, and pool surfaces).

The invention will now be described by way of the following examples. All parts, ratios, percents and amounts stated in the Examples are by weight unless otherwise specified.

EXAMPLES

Test Procedures

Test procedures used in the examples include the following. All ratios and percentages are by weight unless otherwise indicated.

Acid Number

The acid number is determined according to ASTM D1639-90 (1996)e1 entitled, "Test Method for Acid Value of Organic Coating Materials."

Percent by Weight Isocyanate Groups

The percent by weight isocyanate groups present on the polyurethane prepolymer is determined according to ASTM D2572-97 (2003)e1 entitled. "Standard Test Method for Isocyanate Groups in Urethane Materials or Prepolymers."

Preparation of 10 mM Buffer Solution Having a pH of from 4.3 to 4.5

One liter of a 10 milliMolar (mM) buffer solution having a pH of about 4.4 is prepared by placing 1.1 g citric acid and 1.4 g sodium citrate in a flask. A 500 mL volume of tap water is added to the flask and the contents are gently agitated to dissolve all of the solid particles. The volume of the liquid is then adjusted to the 1 liter mark by adding tap water. The solution is gently shaken to homogenize the solution. The pH of the solution is tested using a calibrated pH meter. The resulting buffer solution has a pH from 4.3 and 4.5.

Preparation of Lotion Test Liquid

The lotion test liquid is the aqueous liquid present in the container of PARENT'S CHOICE unscented baby wipes (Walmart Stores Inc., Bentonville, Ark.) and includes 99% water and 1% of a mixture of: propylene glycol, aloe barbadensis leaf juice, tocopheryl acetate, PEG 75 polyethylene glycol, lanolin, disodium cocoamnphodiacetate, polysorbate 20, citric acid, disodium phosphate, disodium EDTA (ethylenediaminetetraacetic acid), methylisothiazolinone, 2-bromo-2-nitropropane-1,3-diol, and iodopropynyl butylcarbamate, and has a pH of from 4.5 to 5.

Dry Binder Integrity Test Method I

A sufficient amount of binder composition is poured on a non-stick pan and left to dry at room temperature to yield a film of about 1.0 g having a thickness of about 1 mm. This process is repeated several times to create several sample specimens. The samples are separated into two groups.

Tap Water Dry Binder integrity Test Method I

In the first group, each dry film sample specimen is transferred to a 1 liter jar containing about 700 g of tap water having a pH of 7, and submerged in the water. The jars are then sealed and the samples are left to soak for two hours.

Aqueous Buffer Dry Binder Integrity Test Method I

In the second group, each dry film sample specimen is transferred to a 1 liter jar containing the above-described 10 mM buffer solution having a pH of from 4.3 to 4.5, and submerged in the solution. The jars are then sealed and the samples are left to soak for two hours.

The jars are then placed on a laboratory shaker (Eberbach Corporation, Ann Arbor, Mich.). The shaker shakes the jars at a frequency of 150 cycles/minute for 10 minutes. The jars are then removed from the machine and opened. The contents of the jars are visually evaluated. The film, or a portion thereof, is retrieved from each the jar and evaluated. Observations regarding the same are recorded.

If the film appears unaltered from its original state, it is recorded as being insoluble.

If the film has broken apart, it is recorded as having disintegrated and lost integrity.

The film is also evaluated to determine if its integrity and cohesive strength have changed relative to its initial state. If the film breaks apart or crumbles when it is removed from the jar, if it has become weak and lacking in cohesive strength compared to its initial state, or if it cannot be removed from the jar because it lacks cohesive strength, it is recorded as having lost integrity.

Dry Binder Integrity Test Method II

An amount of binder composition sufficient to form a dry film having a thickness of about 1 mm is poured on a non-stick surface and left to dry at room temperature for a minimum of 16 hours. The resulting film is then evaluated in this form or further processed by heating in a 150° C. convection oven for 1 minute and then evaluated.

The dried film is evaluated in the following four test liquids: 1) the above-described 10 mM buffer solution having a pH of from 4.3 to 4.5, 2) the above-described lotion test liquid, 3) deionized water, and 4) tap water having a pH of from 6.5 to 9.0.

Approximately 0.2 g of the dried film is put into a screw-top glass jar containing approximately 20 g of a test solution. The jars are then sealed and the samples are left to soak for a minimum of 16 hours (overnight).

After soaking in the test solution, the contents of the jars are visually evaluated. Observations regarding the same are recorded. The film, or a portion thereof, is retrieved from each the jar and evaluated. Observations regarding the same are recorded.

If the film appears unaltered from its original state, it is recorded as being insoluble.

If the film has broken apart, it is recorded as having disintegrated and lost integrity.

The film is also evaluated to determine if its integrity and cohesive strength have changed relative to its initial state. If the film breaks apart or crumbles when it is removed from the jar, if it has become weak and lacking in cohesive strength compared to its initial state, or if it cannot be removed from the jar because it lacks cohesive strength, it is recorded as having lost integrity.

Wipe Integrity Test Method

A number of samples in the form of wipes or a portion of the wipes are obtained. When the size of the wipe is too large to be easily submerged in 700 grams of tap water or the buffer solution, a sample is cut from each wipe. The sample weighs from at least 1 g to no greater than 3 g. If the wipe weighs less than 1 g, multiple wipes can be used to constitute a sample.

The samples are split in two groups.

Tap Water Wipe Integrity Test Method

In the first group, each sample is placed in a 1 liter jar containing 700 g of tap water having a pH of from 6.5 to 9 and submerged in the water. The jars are then sealed and placed on a laboratory shaker (Eberbach Corporation, Ann Arbor, Mich.).

Aqueous Buffer Wipe Integrity Test Method

In the second group, each sample is placed in a 1 liter jar containing 700 g of the above-described 10 mM buffer solution having a from pH 4.3 to 4.5 and submerged in the solution.

The jars are then sealed and placed on the laboratory shaker. The shaker shakes the jars at a frequency of 150 cycles/minute for 10 minutes. After ten minutes the jars are removed from the shaker and opened, and the contents of the jars are evaluated. Observations regarding the same are recorded.

If the wipe appears unaltered from its original state, it is recorded as being insoluble.

If the wipe has broken apart, the wipe is recorded as having disintegrated and lost integrity.

If the wipe is intact or partially intact, the wipe is removed from the jar and rubbed between the fingers and thumb. If the wipe crumbles and breaks apart during the rubbing action, the wipe is recorded as having disintegrated and lost integrity. Observations regarding the results of the rubbing are recorded.

Substrate Integrity Test Method

A number of sample substrates are obtained. When the size of the substrate is too large to be easily submerged in 700 grams of tap water having a pH of from 6.5 to 9 or the buffer solution, a sample is cut from each substrate. The sample weighs from at least 1 g to no greater than 3 g. If the substrate weighs less than 1 g, multiple substrate can be used to constitute a sample.

The samples are split in two groups.

Tap Water Substrate Integrity Test Method

In the first group, each sample is placed in a 1 liter jar containing 700 g of tap water and submerged in the water. The jars are then sealed and placed on a laboratory shaker (Eberbach Corporation, Ann Arbor, Mich.).

Aqueous Buffer Substrate Integrity Test Method

In the second group, each sample is placed in a 1 liter jar containing 700 g of the above-described 10 mM buffer solution having a from pH 4.3 to 4.5 and submerged in the solution. The jars are then sealed and placed on the laboratory shaker. The shaker shakes the jars at a frequency of 150 cycles/minute for 10 minutes. After ten minutes the jars are removed from the shaker and opened, and the contents of the jars are evaluated. Observations regarding the same are recorded.

If the substrate appears unaltered from its original state, it is recorded as being insoluble.

If the substrate has broken apart, the substrate is recorded as having disintegrated and lost integrity.

If the substrate is intact or partially intact, the substrate is removed from the jar and rubbed between the fingers and thumb. If the substrate crumbles and breaks apart during the rubbing action, the substrate is recorded as having disintegrated and lost integrity. Observations regarding the results of the rubbing are recorded.

Control

A Control was prepared in the manner describe under the heading "Preparation of Wipe" in Example 1 above with the exception that the sheet of fibers was sprayed with water instead of a binder composition.

The resulting sheet was tested according to the Wipe Integrity test method. The sheet disintegrated into individual fibers and had no integrity in the buffer solution (i.e., to be intact and strong) and disintegrated into individual fibers and had no integrity in the tap water.

Example 1

Preparation of Polyurethane Prepolymer

A polyurethane prepolymer was prepared by combining 11.45% by weight isophorone diisocyanate, 1.68% by weight dimethylolpropionic acid, 20.69% by weight DESMOPHEN S-102-110 polyol (Bayer, Pittsburgh, Pa.), and 1.2% by weight triethylamine, with mixing, heating the mixture to 80° C., and allowing the components to react for from one to four hours at 80° C. (The weight percents are based on the total weight of the binder composition of Example 1.) The resulting polyurethane prepolymer had 4.5% by weight isocyanate groups and an acid number of 20.

Binder Composition Preparation

A binder composition was prepared by mixing Polyurethane Prepolymer I with water and then transferring the mixture to a stirred dispersion tank. A mixture of monoethanolamine and water was then added to the same dispersion tank. A mixture of diethylenetriamine and water was then added to the same dispersion tank. A mixture of ethylenediamine and water was then added to the same dispersion tank. The resulting mixture was allowed to react for 30 minutes to form a polyurethane dispersion that includes 63.59% by weight water and the reaction product of 35.02% by weight polyurethane prepolymer, 0.41% by weight diethylenetriamine, 0.56% by weight ethylene diamine, and 0.21% by weight monoethanolamine based on the total weight of the resulting binder composition. A solution of 37% by weight formaldehyde in water was then added to the polyurethane dispersion in an amount such that the resulting binder composition includes 0.26% by weight of the 37% by weight formaldehyde solution.

The resulting binder composition had a pH of about 8 and a viscosity of about 25 centipoise at 77° F. (25° C.).

The binder composition was tested according to the Binder Integrity Test Method I. The samples in the tap water turned white, felt gritty, and became crumbly and broke apart. After the sample films had been stored in the tap water for a few weeks, the water in the vessel appeared milky.

The samples in the buffer solution were intact and strong. After the sample films had been stored in the buffer solution for a few weeks, the water in the vessel appeared clear.

Wipe Preparation

The binder composition of Example 1 was sprayed on a 1 g sheet of wood pulp fibers in the form of a fiber mat having an area of 4.5 inch by 9.0 inch. The sheet was dried in an oven at from 125° C. to 130° C. for 2 minutes and then allowed to cool. The resulting wipe included from about 45% by weight to 50% by weight dry binder.

The wipe was tested according to the Wipe Integrity test method. The wipe maintained its integrity in the buffer solution (i.e., to be intact and strong) and lost integrity, disintegrated, and crumbled, in the tap water.

Example 2

Preparation of Polyurethane Prepolymer II

A polyurethane prepolymer was prepared by combining 7.67% by weight isophorone diisocyanate, 0.67% by weight dimethylolpropionic acid, 9.09% RM0294 acid-functional polyol ((H.B. Fuller Company, Vadnais Heights, Minn.), a reaction product of 1 mole of VORANOL 230-238 (Dow Chemical, Midland, Mich.) and 1 mole of phthalic anhydride), 16.85% by weight of VORANOL 220-056 (Dow Chemical, Midland, Mich.), 0.01% by weight of triethylamine and 0.01% by weight of dibutyltindilaurate, with mixing, heating the mixture to 80° C., and allowing the mixture to react for from 1 hour to 4 hours at 80° C. (The weight percents are based on the total weight of the binder composition of Example 2.)

Binder Composition Preparation

A binder composition was prepared by dispersing polyurethane prepolymer II into water containing ammonia with stirring, transferring the mixture to a stirred dispersion tank with mixing, adding a mixture of monoethanolamine and water to the dispersion tank, with mixing, adding a mixture of diethylenetriamine and water to the dispersion tank, with mixing, adding a mixture of ethylenediamine and water to the dispersion tank, with mixing, and allowing the resulting mixture to react for 30 minutes to form a polyurethane dispersion that contains 63.71% by weight of water and the reaction product of 34.3% by weight polyurethane prepolymer II, 0.22% by weight of monoethanolamine, 0.19% by weight of diethylenetriamine, 0.28% by weight ethylenediamine, and 1.04% by weight of a mixture of 25.6% by weight ammonia in water based on the total weight of the resulting binder composition. To the polyurethane dispersion was then added 0.26% by weight of a 37% by weight solution of formaldehyde in water to form the binder composition.

The resulting binder composition had a pH of about 8 and a viscosity of about 25 centipoise at 77° F. (25° C.).

The binder composition was tested according to the Dry Binder Integrity Test Method I. The samples in the tap water turned white, felt gritty, and became crumbly and broke apart. After the sample films have been stored in the tap water for a few weeks, the water in the vessel appeared milky.

The samples in the buffer solution were intact and strong. After the sample films had been stored in the buffer solution for a few weeks, the water in the vessel was clear.

Wipe Preparation

The binder composition of Example 2 was sprayed on a 1 g sheet of wood pulp fibers in the form of a fiber mat having an area of 4.5 inch by 9.0 inch. The sheet was dried in an oven at from 125° C. to 130° C. for 2 minutes and then allowed to cool. The resulting wipe included from about 45% by weight to 50% by weight dry binder.

The wipe was tested according to the Wipe Integrity test method. The wipe maintained its integrity in the buffer solution (i.e., to be intact and strong) and lost integrity, disintegrated, and crumbled in the tap water.

Examples 3-11 and Controls 2-3

Binder compositions were prepared by mixing the binder composition of Example 1 with BAYBOND PU330 polyurethane dispersion (Bayer, Pittsburgh, Pa.) in the ratios set forth in Table 1. The binder compositions of Examples 3-11 and Controls 2-3 were then tested according to the Dry Binder Integrity Test Method II and the results and observations of the test samples are set forth in Table 1.

TABLE 1

| | | Control | | 10 mM Buffer Solution (pH 4.5*) | | Lotion (pH 4.5) | |
|---|---|---|---|---|---|---|---|
| Sample | Blend | Room Temp | 150° C. | Room Temp | 150° C. | Room Temp | 150° C. |
| Example 3 | 100/0 | Tough film | Tough film | Strong film; stretched | Strong film, stretched | Strong film, stretched | Strong film, stretched |
| Example 4 | 99.5/0.5 | Tough film, | Very tough film, stretched | Strong film | Strong film | Strong film, stretched | Strong film, stretched |

TABLE 1-continued

| | | | | | | | |
|---|---|---|---|---|---|---|---|
| Example 5 | 99/1 | Tough film | Very tough film, did not stretch | Strong film, Stretched more than control | Stretched more than control | Stretched more than control | stretched some; tough film |
| Example 6 | 97/3 | Tough film, stretched a little | Very tough film, barely stretched | Tough film, stretched | Tough film, did not stretch | Tough film, stretched | Tough film, stretched |
| Example 7 | 95/5 | Tough, stretched slightly | Tough, stretched slightly | Strong film, stretched | Very strong, stretched | Strong, stretched | Very strong, stronger than in buffer solution |
| Example 8 | 90/10 | Strong, stretched then ripped | Strong, stretched | Strong, stretched, a little weaker than lotion | Strong, stretched, a little weaker than lotion | Very strong, stretched | Very strong, stretched |
| Example 9 | 80/20 | Strong, stretched slightly | Strong, stretched slightly | Strong film, stretched | Strong film, stretched | Strong film, stretched | Strong film, stretched |
| Example 10 | 70/30 | Strong, stretched slightly | Strong, stretched slightly | Strong film, stretched then broke, stronger than in lotion | Strong film, stretched then broke, stronger than in lotion | Strong film, stretched then broke | Strong film, stretched then broke |
| Example 11 | 60/40 | Strong, Stretched | Strong, stretched then broke | Weak film, stretched, then broke; a little stronger than in lotion | Weak film, stretched and then broke; A little stronger than in lotion | Weak film stretched and then broke | Weak film, stretched a little and then broke |
| Control 2 | 50/50 | Strong, Stretched, then broke | Strong, stretched then broke | Weak film, tore easily | Weak film, tore easily | Weak film, tore easily | Weak film, tore easily |
| Control 3 | 0/100 | Broke easily | Broke easily | Gel-like, very weak, fell apart | Gel-like, very weak, fell apart | Gel-like, very weak, fell apart | Gel-like, very weak, fell apart |

| | Deionized Water (DI) | | Tap Water | |
|---|---|---|---|---|
| Sample | Room Temp | 150° C. | Room Temp | 150° C. |
| Example 3 | Weak, broke easily | Weak, broke easily | Weak, broke, stronger than DI | Weak, broke, stronger than DI |
| Example 4 | disintegrated | Crumbled, weak | disintegrated | Weak, ripped, stronger than in DI |
| Example 5 | disintegrated | disitegrated | Very weak | Crumbled, very weak |
| Example 6 | disintegrated | disintegrated | Very weak | Easy to rip film |
| Example 7 | No strength, weak, gel-like | Very weak, No strength, | Very low strength, fell apart | Broke apart easily, more strength than DI |
| Example 8 | Very weak, no strength | Very weak, No strength, can't lift pieces out of jar | Very weak, No strength, can't lift pieces out of jar | Very weak, broke apart |
| Example 9 | No strength, fell apart | No strength, fell apart | Very weak film, easily fell apart | Very weak film, easily tore, gel-like |
| Example 10 | No strength | No strength | Film fell apart | Film fell apart |
| Example 11 | Film fell apart | Film fell apart | Weak film, easily tore | Weak film, easily tore |
| Control 2 | Very weak film, fell apart | Very weak film, fell apart | Weak film, tore easily, tore slightly easier than in lotion | Weak film, tore easily, tore slightly easier than in lotion |
| Control 3 | Gel-like, very weak, fell apart | Gel-like, very weak, fell apart | Gel-like, very weak, fell apart | Gel-like, very weak, fell apart |

*= The actual pH of the buffer solution was 4.52.

All patents and references referred to herein are incorporated herein.

Other embodiments are within the claims. In one embodiment, for example, the wipe is packaged in a container, which stores the wipe or multiple wipes (e.g., a roll of wipes or a stack of wipes) until use. A storage medium optionally is present in the container and the wipe optionally is saturated with the storage medium.

The wipe can be of any dimension and any shape including, e.g., rectangular, square, circular, and oval.

In addition, although the substrate that includes fibers and the binder composition has been described above as being in the form of a wipe, the substrate can be in the form of a variety of articles and can be a component of a variety of articles including, e.g., a woven web, nonwoven web, pad, sanitary napkin, diaper, training pant, incontinence article, container (e.g., box, bag, and envelope) and combinations thereof), filter (e.g., air filter, oil filter, and gasoline filter), ostomy bag, disposable garment, disposable surgical gown, face mask, insert for an absorbent article, shoe insert, antiperspirant patch, breast pad, helmet liner, wound dressing, sterile wrap, cover for an automobile, disposable ground cover, blanket, table cloth (e.g., operating table sheet, examination table sheet, and mortuary sheet) and combinations thereof.

The dried binder can also be provided in a variety of forms including, e.g., a film, particles (e.g., granules and powder), fibers, webs (e.g., woven and nonwoven webs), and composites and combinations thereof, and optionally combined with other components to form films, fibers, webs (e.g., woven and nonwoven webs), composites, and combinations thereof. The other components with which the binder can be combined can be in a variety of forms including, e.g., fibers, grains, granules, powders, and made from a variety of materials including, e.g., polymers (e.g., synthetic (e.g., thermoplastic polymers, superabsorbent polymers, and combinations thereof) and natural), cellulose, polylactic acid polymer, biodegradable materials, metals, dirt, and combinations thereof.

What is claimed is:

1. A flushable article comprising:
    a substrate comprising fibers; and
    a dried binder composition in contact with the fibers, the dried binder composition having been derived from an aqueous composition comprising polyurethane,
    the article being insoluble in water having a pH of no greater than 6 and disintegrating in water having a pH of at least 6.5.

2. The article of claim 1, wherein the article is in the form of a wipe.

3. The wipe of claim 2 further comprising an aqueous medium in contact with the substrate, the medium having a pH no greater than 6.

4. The wipe of claim 3, wherein the medium comprises a lotion.

5. The wipe of claim 2, wherein the fibers comprise at least one of wood pulp, cellulose, polyethylene, polypropylene, polyester, polyamide, and polylactic acid.

6. The wipe of claim 2, wherein the wipe comprises at least 5% by weight binder based on the weight of the binder and the substrate.

7. The wipe of claim 2, wherein the dried binder composition is insoluble in water having a pH no greater than 5.5.

8. The wipe of claim 2, wherein the dried binder composition is derived from an anionic polyurethane dispersion.

9. The wipe of claim 2, wherein the dried binder composition comprises a polyurethane comprising the reaction product of
    an acid-functional polyurethane prepolymer,
    a chain extending agent comprising a polyamine, and
    a chain terminating agent comprising a monoamine.

10. The wipe of claim 9, wherein the polyurethane prepolymer has a residual isocyanate functionality of from 2% by weight to 6% by weight, and the binder composition is formed from the monoamine in an amount such that the ratio of amine groups in the monoamine to isocyanate groups in the polyurethane prepolymer is from 0.01:1 to 0.8:1.

11. The wipe of claim 2, wherein the dried binder composition comprises a polyurethane comprising the reaction product of
    an acid-functional polyurethane prepolymer at least a portion of which is in a form selected from the group consisting of an alkali metal salt, a salt of a tertiary amine, an ammonium salt, and combinations thereof,
    a chain extending agent comprising a polyamine, and
    a chain terminating agent comprising a monoamine.

12. The wipe of claim 2, wherein the dried binder composition comprises a polyurethane comprising the reaction product of
    a polyurethane prepolymer,
    a polyamine,
    a monoamine, and
    a tertiary amine.

13. A packaged article comprising:
    a container;
    an aqueous medium disposed in the container; and
    the wipe of claim 2 disposed in the container and saturated with the aqueous medium.

14. The packaged article of claim 13, wherein the dried binder composition is derived from an anionic polyurethane dispersion.

15. A method of making a flushable article, the method comprising:
    applying an aqueous binder composition comprising polyurethane on fibers, a substrate comprising fibers, or both fibers and a substrate comprising fibers, the binder composition, when dry, being insoluble in water having a pH no greater than 6 and disintegrating in water having a pH greater than 6.5;
    drying the binder composition; and
    optionally forming a substrate from the fibers.

16. The method of claim 15, wherein the article disintegrates in tap water when tested according to the Substrate Integrity test method.

17. The method of claim 15 further comprising contacting the substrate with an aqueous medium having a pH no greater than 6.

18. The method of claim 15, wherein the aqueous binder composition comprises a first anionic polyurethane dispersion comprising the reaction product of
    a polyurethane prepolymer,
    a polyamine, and
    a monoamine.

19. The method of claim 18, wherein the aqueous binder composition further comprises a second anionic polyurethane dispersion comprising an alkali metal salt of a sulfonic acid.

20. The method of claim 15, wherein the article is a wipe and the substrate is a sheet.

21. The method of claim 15, wherein the aqueous binder composition is derived from an anionic polyurethane dispersion.

22. A flushable article comprising:
    a substrate comprising fibers; and
    a dried binder in contact with the fibers, the dried binder composition being derived from an aqueous composition comprising polyurethane, being insoluble in water having a pH of no greater than 6, and disintegrating in water having a pH of at least 6.5.

23. The article of claim 22, wherein the dried binder composition is insoluble in water having a pH of no greater than 5.5.

24. The article of claim 22, wherein the dried binder composition disintegrates in water having a pH of at least 7.

25. A multi-component article comprising the article of claim 22, the multi-component article being in the form of a diaper, sanitary napkin, sheet, training pants, incontinence articles, a container, filter, ostomy bag, garment, surgical gown, face mask, insert for an absorbent article, shoe insert, antiperspirant patch, breast pad, helmet liner, wound dressing, sterile wrap, automobile cover, ground cover, blanket, table cloth, or a combination thereof.

26. The article of claim 22, wherein the dried binder composition is derived from an anionic polyurethane dispersion.

27. A flushable article comprising:
a substrate comprising fibers; and
a dried binder composition in contact with the fibers, the dried binder composition
being derived from an aqueous composition comprising polyurethane,
being insoluble in water having a pH of no greater than 6,
having an initial state, and,
when tested in tap water according to the Tap Water Dry Binder Integrity Test Method I, disintegrating, losing integrity relative to the initial state, decreasing in cohesive strength relative to the initial state, or a combination thereof.

28. The article of claim 27, wherein the dried binder composition is derived from an anionic polyurethane dispersion.

29. A dried binder composition comprising:
the reaction product of a polyurethane prepolymer, a chain extending agent comprising a polyamine, and a chain terminating agent comprising a monoamine,
the dried binder composition
being in a form selected from the group consisting of fibers, filaments, granules, particles, powder, and combinations thereof, and
being insoluble in water having a pH of no greater than 6, and
disintegrating in water having a pH of at least 6.5.

30. A flushable article comprising:
a substrate comprising fibers; and
a dried binder composition derived from an anionic polyurethane dispersion, the dried binder composition being in contact with the fibers,
the article being insoluble in water having a pH of no greater than 6 and disintegrating in water having a pH of at least 6.5.

31. The article of claim 30 further comprising an aqueous medium in contact with the substrate, the medium having a pH no greater than 6.

32. The article of claim 30, wherein the medium comprises a lotion.

33. The article of claim 30, wherein the substrate comprises at least 5% by weight binder based on the weight of the binder and the substrate.

34. The article of claim 30, wherein the dried binder composition is insoluble in water having a pH no greater than 5.5.

35. The article of claim 30, wherein the dried binder composition comprises a polyurethane comprising the reaction product of
an acid-functional polyurethane prepolymer,
a chain extending agent comprising a polyamine, and
a chain terminating agent comprising a monoamine.

36. The article of claim 30, wherein the dried binder composition comprises a polyurethane comprising the reaction product of
an acid-functional polyurethane prepolymer at least a portion of which is in a form selected from the group consisting of an alkali metal salt, a salt of a tertiary amine, an ammonium salt, and combinations thereof,
a chain extending agent comprising a polyamine, and
a chain terminating agent comprising a monoamine.

37. The article of claim 30, wherein the dried binder composition comprises a polyurethane comprising the reaction product of
a polyurethane prepolymer,
a polyamine,
a monoamine, and
a tertiary amine.

38. A method of making a flushable article, the method comprising:
applying an aqueous binder composition on fibers, a substrate comprising fibers, or a combination thereof, the binder composition comprising a first anionic polyurethane dispersion comprising the reaction product of a polyurethane prepolymer, a polyamine, and a monoamine, the binder composition, when dry, being insoluble in water having a pH no greater than 6 and disintegrating in water having a pH greater than 6.5;
drying the binder composition; and
optionally forming a substrate from the fibers.

39. The method of claim 38, wherein the article disintegrates in tap water when tested according to the Substrate Integrity test method.

40. The method of claim 38 further comprising contacting the substrate with an aqueous medium having a pH no greater than 6.

41. The method of claim 38, wherein the aqueous binder composition further comprises a second anionic polyurethane dispersion comprising an alkali metal salt of a sulfonic acid.

* * * * *